United States Patent
Hwang et al.

(10) Patent No.: US 9,846,144 B2
(45) Date of Patent: Dec. 19, 2017

(54) APPARATUS AND METHOD FOR DETECTING DEFECT OF PRESS PANEL

(71) Applicants: Hyundai Motor Company, Seoul (KR); Kia Motors Corporation, Seoul (KR); UNIST Academy-Industry Research Corporation, Ulsan (KR)

(72) Inventors: Jae Ryeon Hwang, Ulsan (KR); ByungHun Kim, Ulsan (KR); Franklin Bien, Ulsan (KR); Hyon Gi Yoo, Seoul (KR); Chan Woo Jeong, Seoul (KR); Nguyen Ngoc Quang, Ulsan (KR); Liu Zhenyi, Korea (RE); Seul Ki Rom Kim, Gwangju (KR)

(73) Assignees: Hyundai Motor Company, Seoul (KR); Kia Motors Corporation, Seoul (KR); UNIST Academy-Industry Research Corporation, Ulsan (KR)

( * ) Notice: Subject to any disclaimer, the term of this patent is extended or adjusted under 35 U.S.C. 154(b) by 258 days.

(21) Appl. No.: 14/873,728

(22) Filed: Oct. 2, 2015

(65) Prior Publication Data
US 2016/0097745 A1  Apr. 7, 2016

(30) Foreign Application Priority Data
Oct. 2, 2014 (KR) .......................... 10-2014-0133224

(51) Int. Cl.
G01N 29/14 (2006.01)
G01N 29/44 (2006.01)

(52) U.S. Cl.
CPC ......... *G01N 29/14* (2013.01); *G01N 29/4427* (2013.01); *G01N 29/4436* (2013.01);
(Continued)

(58) Field of Classification Search
CPC .............. G01N 29/14; G01N 29/4427; G01N 29/4436; G01N 2291/2632; G01N 2291/0234
(Continued)

(56) References Cited

U.S. PATENT DOCUMENTS 5,142,916 A * 9/1992 Yamaguchi ............. G01M 7/00
73/162
6,386,038 B1 * 5/2002 Lewis, III .............. G01N 29/14
702/39
(Continued)

FOREIGN PATENT DOCUMENTS

JP  2004-263775 A  9/2004
JP  2007-044716 A  2/2007
(Continued)

*Primary Examiner* — J M Saint Surin
(74) *Attorney, Agent, or Firm* — Mintz Levin Cohn Ferris Glovsky and Popeo, P.C.; Peter F. Corless (57) ABSTRACT

An apparatus for detecting a defect of a press panel includes: an acoustic emission sensor unit configured to detect at least one elastic wave signal emitted from the press panel as a detection target during press work, a period measurer configured to measure a period as a section in which there are consecutive signals with a greater voltage than a threshold voltage among the at least one detected signals, and a defect existence determination unit configured to determine that a defect is generated in the press panel when the measured period is greater than a first reference value, and to determine that the press panel is in a normal state when the measured period is smaller than a second reference value which is smaller than the first reference value.

11 Claims, 7 Drawing Sheets

(52) U.S. Cl.
CPC ............... *G01N 2291/0234* (2013.01); *G01N 2291/2632* (2013.01)

(58) Field of Classification Search
USPC .......................................................... 73/587
See application file for complete search history.

(56) References Cited

U.S. PATENT DOCUMENTS

| | | | |
|---|---|---|---|
| 6,591,681 B1 * | 7/2003 | Shimada ............. | G01N 29/045 73/600 |
| 7,939,780 B2 * | 5/2011 | Murao ................... | B23K 26/03 219/121.62 |

FOREIGN PATENT DOCUMENTS

| | | | |
|---|---|---|---|
| JP | 2010-181203 A | | 8/2010 |
| JP | 2013160500 | * | 8/2013 |
| KR | 10-0309280 B | | 4/2002 |
| KR | 101404027 | * | 6/2014 |
| WO | 2011/001536 A1 | | 1/2011 |

* cited by examiner

APPARATUS AND METHOD FOR DETECTING DEFECT OF PRESS PANEL

CROSS-REFERENCE TO RELATED APPLICATION

This application claims priority to and the benefit of Korean Patent Application No. 10-2014-0133224 filed in the Korean Intellectual Property Office on Oct. 2, 2014, the entire contents of which are incorporated herein by reference.

BACKGROUND OF THE DISCLOSURE (a) Technical Field

The present disclosure relates generally to an apparatus and method for detecting a defect of a press panel. More particularly, the present disclosure relates to an apparatus and method for detecting a defect of a press panel, for determining whether a corresponding panel is defective using an elastic wave signal emitted during press work for manufacturing the panel.

(b) Description of the Related Art

In order to estimate soundness of materials or products, non-destructive inspection that does not affect a material or shape and dimension is often used. Examples of non-destructive inspection include macroscopic inspection, ultrasonic wave inspection, radiation inspection, and acoustic inspection. Among the examples listed above, macroscopic inspection is a method for checking whether there is an abnormality, e.g., whether there is a defect or whether a member is deformed by unassisted visual inspection, and for determining whether there is a defect by absorbing an inspection target by an inspector using equipment such as a magnifying glass. The macroscopic inspection does not require many inspection devices, and thus, the method may be simply performed; however, the method requires an inspector with sufficient knowledge and ability to perform the inspection. Whether a press panel is defective can be determined using the macroscopic inspection, and whether a detection target is defective is inspected by alternately monitoring two mirrors, which reflect upper and lower surfaces of the detection target that passes at a predetermined speed, by an inspector who stands in front of the two mirrors.

In addition, ultrasonic wave inspection inspects whether an internal part of a detection target is defective using properties whereby an ultrasonic wave beam applied to the detection target is reflected where an internal defect occurs. Information about whether there is a defect and a location of the defect may be acquired using intensity of the reflected ultrasonic wave energy and reflection time.

Meanwhile, radiation inspection for inspecting an internal defect of a product using X-rays or radioisotope is often used to detect a defect of a weld zone or a casting or a defect according to a change in radiation intensity on a radiography image acquired by irradiating a detection target with radiation. Although radiation inspection is a non-destructive inspection technique that is most frequently used in South Korea, the amount of transmitted radiation during an inspection for defect detection is 5 mSv that corresponds to 50 times higher than radiation used for an X-ray examination in hospitals. Accordingly, an inspector is at a risk for being exposed to radiation during the inspection and thus needs to pay particular attention.

Lastly, acoustic inspection inspects a defect using an elastic wave signal that is generated while a solid material is deformed or destroyed. In acoustic inspection, whether a defect is inspected while applying elastic stress to a detection target. A plurality of acoustic emission sensors may be installed in the detection target, a crack initiation site may be estimated via collected signals, and various information items such as the shape or degree of crack may be interpreted. In particular, acoustic inspection may enable wide area inspection compared with other non-destructive inspection and may also enable inspection while equipment or a structure is used. In addition, the acoustic inspection may enable real-time measurement and detect a defect location. However, signals collected through the acoustic emission sensor need to be interpreted dependent upon the inspector's experience, and background noise processing highly affects the accuracy of inspection.

The above information disclosed in this Background section is only for enhancement of understanding of the background of the disclosure, and therefore, it may contain information that does not form the related art that is already known in this country to a person of ordinary skill in the art.

SUMMARY OF THE DISCLOSURE

The present disclosure has been made in an effort to provide an apparatus and method for detecting a defect of a press panel, having advantages of determining whether there is a defect of the corresponding panel using an elastic wave signal emitted during press work for manufacturing the panel.

According to embodiments of the present disclosure, an apparatus for detecting a defect of a press panel includes: an acoustic emission sensor unit configured to detect at least one elastic wave signal emitted from the press panel as a detection target during press work, a period measurer configured to measure a period as a section in which there are consecutive signals with a greater voltage than a threshold voltage among the at least one detected signals, and a defect existence determination unit configured to determine that a defect is generated in the press panel when the measured period is greater than a first reference value, and to determine that the press panel is in a normal state when the measured period is smaller than a second reference value which is smaller than the first reference value.

The first reference value and the second reference value may be determined using a period value pre-measured from a plurality of press panels as a comparison target, and the first reference value and the second reference value may refer to a value of a boundary line on distribution of a period of a press panel in which a defect is generated from the comparison target and a period of a press panel in a normal state from the comparison target.

The apparatus may further include an extractor configured to extract from the at least one detected signals: i) at least one parameter among the number of pulses with a greater output voltage than the threshold voltage, ii) energy as the sum of areas of pulses with a greater output voltage than a threshold voltage, and iii) an average frequency generated during the period.

The defect existence determination unit may be further configured to determine whether the press panel is defective using the at least one extracted parameter when the measured period has a value between the first reference value and the second reference value.

The defect existence determination unit may be further configured to determine that a defect is generated in a corresponding press panel when the number of pulses and the energy are higher than a reference number among the extracted parameter, and determine that a defect is generated in the corresponding press panel when the average frequency generated during the period is lower than a reference number.

Furthermore, according to embodiments of the present disclosure, a method for detecting a defect using a press panel defect detection apparatus includes: detecting at least one elastic wave signal emitted from the press panel as a detection target during press work, measuring a period as a section in which there are consecutive signals with a greater voltage than a threshold voltage among the at least one detected signals, determining that a defect is generated in the press panel when the measured period is greater than a first reference value, and determining that the press panel is in a normal state when the measured period is smaller than a second reference value which is smaller than the first reference value.

The first reference value and the second reference value may be determined using a period value pre-measured from a plurality of press panels as a comparison target, and the first reference value and the second reference value may refer to a value of a boundary line on distribution of a period of a press panel in which a defect is generated from the comparison target and a period of a press panel in a normal state from the comparison target.

The method may further include extracting from the at least one detected signal: i) at least one parameter among the number of pulses with a greater output voltage than the threshold voltage, ii) energy as the sum of areas of pulses with a greater output voltage than a threshold voltage, and iii) an average frequency generated during the period.

The determining that the defect is generated may include determining whether the press panel is defective using the at least one extracted parameter when the measured period has a value between the first reference value and the second reference value.

The determining that the defect is generated may further include determining that a defect is generated in a corresponding press panel when the number of pulses and the energy are higher than a reference number among the extracted parameter, and determining that a defect is generated in the corresponding press panel when the average frequency generated during the period is lower than a reference number.

Furthermore, according to embodiments of the present disclosure, a non-transitory computer readable medium containing program instructions for detecting a defect of a press panel, the computer readable medium includes: program instructions that measure a period as a section in which there are consecutive signals with a greater voltage than a threshold voltage among at least one elastic wave signal emitted from the press panel detected as a detection target during press work, program instructions that determine that a defect is generated in the press panel when the measured period is greater than a first reference value, and program instructions that determine that the press panel is in a normal state when the measured period is smaller than a second reference value which is smaller than the first reference value.

Accordingly, according to the present disclosure, the apparatus and method for detecting a defect of a press panel is used so as to simply detect a defect generated during press work, and whether a defect is generated is more accurately determined with respect to a detection target, defect determination of which is ambiguous, using a parameter.

DETAILED DESCRIPTION OF THE EMBODIMENTS

The present disclosure will be described more fully hereinafter with reference to the accompanying drawings, in which exemplary embodiments of the disclosure are shown. As those skilled in the art would realize, the described embodiments may be modified in various different ways, all without departing from the spirit or scope of the present disclosure. Accordingly, the drawings and description are to be regarded as illustrative in nature and not restrictive. Like reference numerals designate like elements throughout the specification.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It is understood that one or more of the below methods, or aspects thereof, may be executed by at least one control unit. The term "control unit" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the control unit in conjunction with one or more other components, as would be appreciated by a person of ordinary skill in the art.

Furthermore, the control unit of the present disclosure may be embodied as non-transitory computer readable media on a computer readable medium containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The present disclosure will now be described more fully with reference to the accompanying drawings, in which embodiments of the disclosure are shown.

Figure 1:
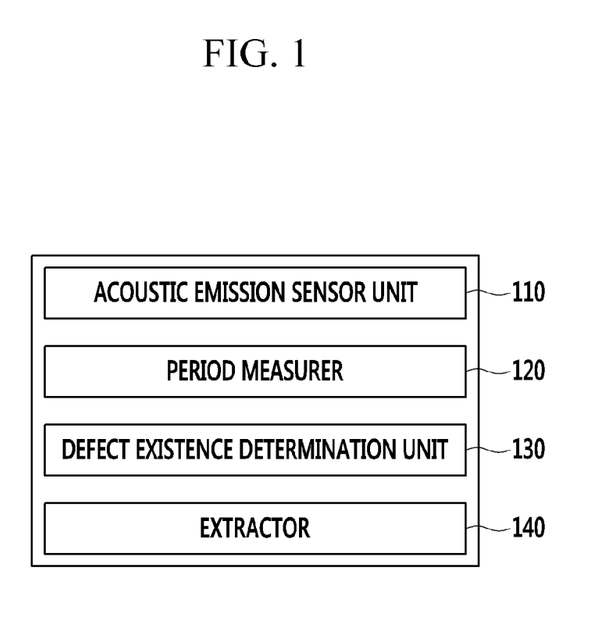
FIG. 1 is a block diagram illustrating a structure of a press panel defect detection apparatus according to embodiments of the present disclosure.

FIG. 1 is a block diagram illustrating a structure of a press panel defect detection apparatus 100 according to embodiments of the present disclosure.

As shown in FIG. 1, the press panel defect detection apparatus 100 includes an acoustic emission sensor unit 110, a period measurer 120, an extractor 140, and a defect existence determination unit 130.

First, the acoustic emission sensor unit 110 detects an elastic wave emitted during press work from a press panel as a detection target. When a metallic panel is processed using a press machine, elastic waves are emitted while strain energy that is locally formed in the panel is remarkably released. In this case, the emitted elastic wave is an acoustic emission (AE) signal, and the acoustic emission sensor unit 110 detects the AE signal using an AE sensor.

In addition, the acoustic emission sensor unit 110 is attached to a surface of the press panel as a defect detection target so as to detect an AE signal. When an AE signal is emitted from the press panel due to deformation by destruction, the acoustic emission sensor unit 110 detects slight dynamic displacement generated due to waves that reach the surface of the press panel from a source in the press panel and converts the detected signal into an electrical signal. In addition, the AE signal may also be detected in a non-contact method without contacting a detection target using a non-contact AE sensor.

Even the slightest change in a solid such as a press panel, for example, dislocation, generation and growth of shattered cracks, and melting and solidification may be captured using the AE signal. When a press panel is sheared using a press machine, the press panel is put into a die, or the press panel is bent by applying bending stress to the press panel, an AE signal is emitted from the press panel. In this case, the emitted AE signal is detected by the acoustic emission sensor unit 110 and is converted into an electrical signal.

In addition, the period measurer 120 measures a period as a section in which there are consecutive signals with a greater voltage than a threshold voltage among detected signals. Among signals converted into electrical signals, signals with a voltage equal to or greater than a threshold voltage are extracted, and among the extracted signals, a section in which there are consecutive signals with a greater voltage than a threshold voltage is determined. In addition, a period as a length of the section is measured.

When signals detected from a press panel as a detection target contains an AE signal, the detected signal contains many pulses with a high voltage. Accordingly, information about a period as a section in which there are consecutive pulses with a greater voltage than a threshold voltage may be extracted, and whether a defect is generated in a corresponding press panel may be determined using the period information.

Then, when a measured period is greater than a first reference value, the defect existence determination unit 130 determines that a defect is generated in the press panel, and when the measured period is smaller than a second reference value, the defect existence determination unit 130 determines that the press panel is in a normal state. For convenience of description, a reference value for determining a defective press panel in a period value is referred to as the first reference value, and a reference value for determining a press panel in a normal state is referred to as the second reference value. In addition, the first reference value is greater than the second reference value.

When a period of a press panel as a detection target is equal to or less than the first reference value and equal to or more than the second reference value, it is difficult to determine whether there is a defect using only a period. In this case, the defect existence determination unit 130 may two-dimensionally determine whether the corresponding press panel is defective using a parameter extracted from the extractor 140 to be described later.

Lastly, the extractor 140 extracts at least one parameter among the number of pulses with a greater output voltage than a threshold voltage, energy as the sum of areas of pulses with a greater output voltage than a threshold voltage, and an average frequency generated during a period, from the detected signals.

In the case of a press panel with a period smaller than the first reference value and greater than the second reference value, it is difficult to determine whether the press panel is defective using only the period. In this case, the defect existence determination unit 130 may two-dimensionally determine whether the press panel is defective, using the extracted parameter and the period.

For example, when a period is greater than the second reference value and smaller than the first reference value, the number of pulses with a greater voltage than a threshold voltage is greater than a reference value, or a value of energy is greater than a reference value, the corresponding press panel is determined to be defective. In addition, when the average frequency is smaller than a reference value, the corresponding press panel may be determined to be defective.

Hereinafter, a method for detecting a defect of a press panel according to embodiments of the present disclosure will be described in more detail with reference to FIGS. 2 to 5.

Figure 2:
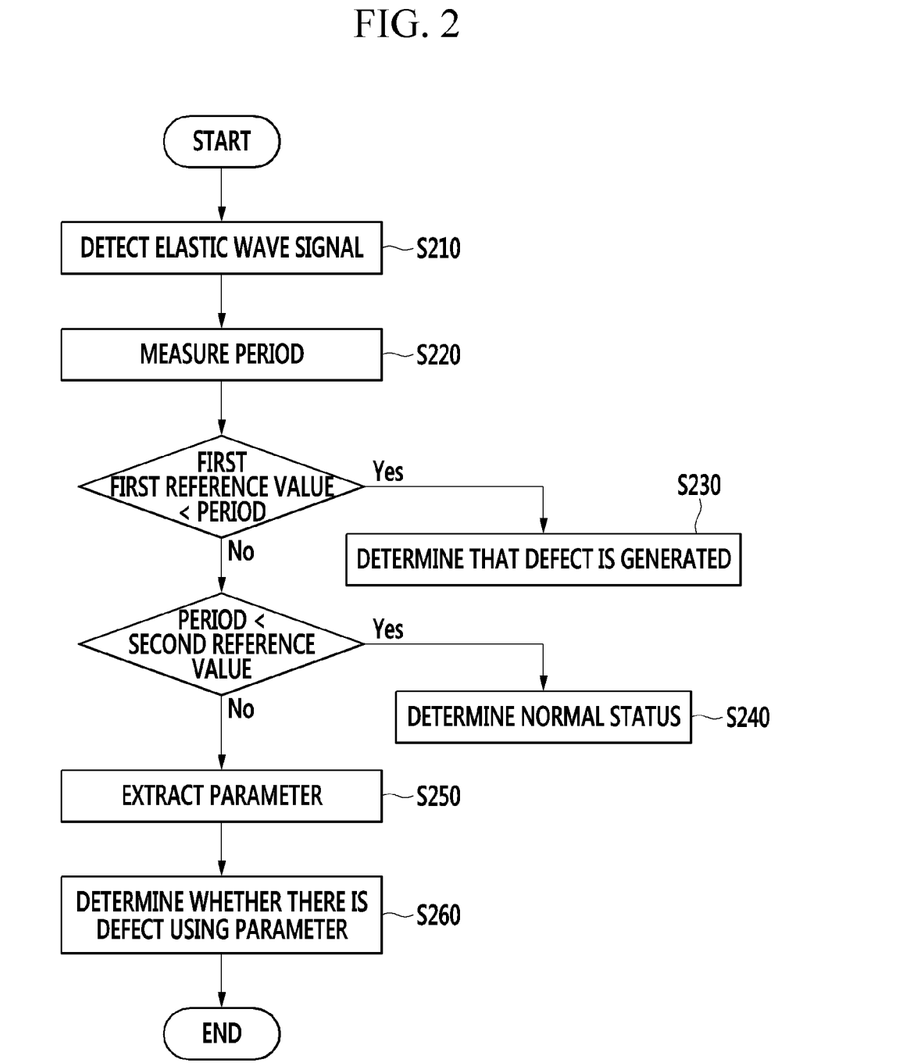
FIG. 2 is a flowchart for explanation of a method for detecting a defect of a press panel according to embodiments of the present disclosure.

FIG. 2 is a flowchart for explanation of a method for detecting a defect of a press panel according to embodiments of the present disclosure.

Figure 3:
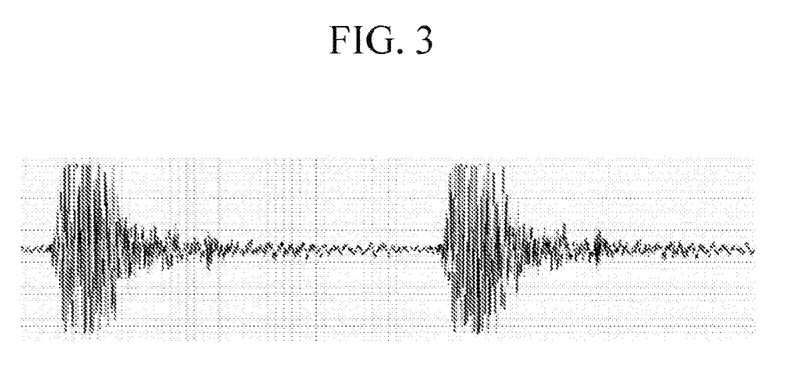
FIG. 3 is a diagram illustrating a signal received in operation S210 according to embodiments of the present disclosure.

First, the acoustic emission sensor unit 110 detects an AE signal from a press panel as a detection target (S210). In this regard, FIG. 3 is a diagram illustrating a signal received in operation S210 according to embodiments of the present disclosure. As shown in FIG. 3, the acoustic emission sensor unit 110 converts the signal detected from the press panel into an electrical signal. As such, change in a voltage value according to time may be achieved. In FIG. 3, a time point with high amplitude refers to a time point when a pressure is applied to the press panel. One period of the detected signal may be analyzed to detect a defect contained in the corresponding press panel.

Referring again to FIG. 2, the period measurer 120 then measures a period of a section in which there are consecutive pulses with a greater voltage than a threshold voltage, from the detected signal (S220). Here, the threshold voltage refers to a value of a voltage for differentiating other signals from pulses of an AE signal. Through a signal with a voltage equal to or greater than a threshold voltage, the defect existence determination unit 130 to be described later may determine whether there is a defect in a press panel from which the corresponding signal is emitted.

Figure 4:
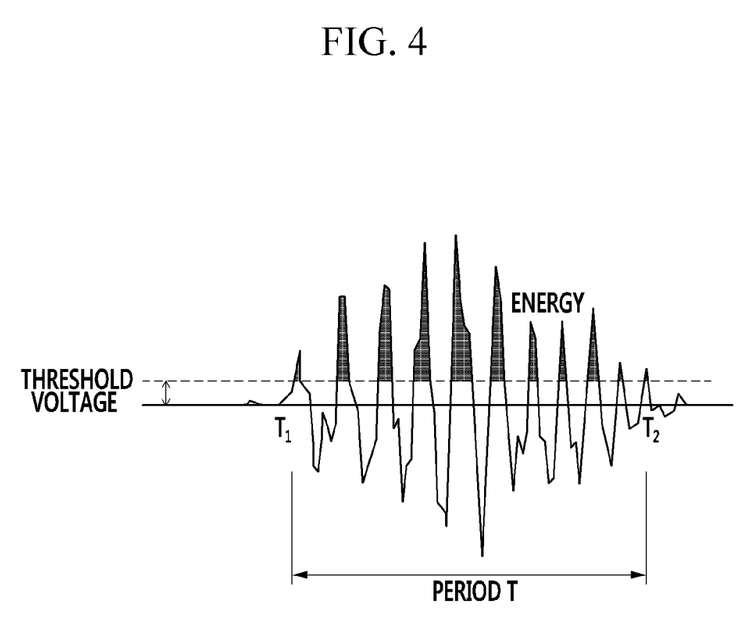
FIG. 4 is a diagram for explanation of operations S220 and S250 according to embodiments of the present disclosure.

FIG. 4 is a diagram for explanation of operations S220 and S250 according to embodiments of the present disclosure. As shown in FIG. 4, the period measurer 120 measures a period of a section in which there are consecutive pulses with a greater voltage than a threshold voltage, from the signal detected in operation S210.

In addition, the defect existence determination unit 130 determines whether the corresponding press panel is defective using the measured period value. When the period is greater than first reference value, the defect existence determination unit 130 determines that a defect is generated in the corresponding press panel (S230).

When the period is smaller than the second reference value smaller than the first reference value, the defect existence determination unit 130 determines that the corresponding press panel is in a normal state (S240).

Here, the first reference value and the second reference value are determined using period values that are pre-measured from a plurality of press panels. Operations S210 and S220 may be performed on a plurality of defective press panels and a plurality of normal press panels to form period values as a database. Two reference values for differentiating between a normal press panel and a defective press panel are set through the period values formed as a database.

When a period is smaller than the first reference value and greater than the second reference value, whether there is a defect is not determined using only the period. In this case, a parameter may be determined via operation S250 to be described later and whether a defect is generated in the corresponding press panel may be determined using the extracted parameter.

Then, the extractor 140 extracts a parameter from the signal detected in operation S220 (S250). The extractor 140 extracts a parameter from signals during a period measured in operation S220 and extracts at least one parameter among the number of pulses, energy, and average frequency. The number of pulses refers to the number of pulses with a greater voltage than a threshold voltage and the energy refers to the sum of areas of pulses with a greater value than a threshold voltage. In addition, the average frequency refers to frequency average of signals generated during the period.

As shown in FIG. 4, the extractor 140 counts the number of pulses with a greater voltage than a threshold voltage to calculate the number of the pulses and calculates energy using the sum of areas with a voltage equal to or greater than a threshold voltage among the counted pulses. In addition, the extractor 140 calculates an average frequency of signals generated during a period.

Lastly, the defect existence determination unit 130 determines whether the corresponding press panel is defective using the measured period and the extracted parameter (S260). The defect existence determination unit 130 determines that a defect is generated in a press panel with a great number of pulses or high energy and determines that a defect is generated in a press panel with a low average frequency, among the extracted parameters.

Hereinafter, a result of the simulation using press panel defect detection apparatuses according to embodiments of the present disclosure will be described in detail with reference to FIGS. 5 and 6. As shown in Table 1, simulation proceeds with respect to 65 press panels and press panels are differentiated by sequentially denoting the press panels by #1 to #65 as a sampling order of the press panels.

TABLE 1

| Sample No. | Pressure (tons) | Frictional force | Final Status |
| --- | --- | --- | --- |
| 1-60 | 170 | — | Unconfirmed |
| 61 | 240 | | Normal |
| 62 | | Occurrence (Used sandpaper) | Breakage |
| 63 | 170 | | Crack |
| 64 | | | |
| 65 | | | Normal |

As shown in Table 1, press work for applying a pressure of 170 tons is performed on press panels #1 to #60, a pressure of 240 tons is applied to press panels #61 and #62, and a pressure of 170 tons is applied to press panels #63 to #65. Frictional force generated in an actual press work site is not generated in press panels #1 to #61. Accordingly, status confirmation of a press panel is meaningless.

In order to reproduce frictional force generated in an actual press work site, press work is performed on press panels #62 to #65 using a sand paper. Heat is generated in a press machine due to press work that is repeatedly performed at an actual press work site and acts as frictional force in a press panel. The sum of pressure applied in a press work process and frictional force generated due to heat generated in a press machine may be applied to an actual press panel. In addition, the generated frictional force is a main factor for generating a defect in a press panel. Accordingly, in the present simulation, frictional force generated in an actual press work site is reproduced using a sand paper.

As a checking result of the press worked press panels #63 to #65, a defect is detected from press panels #63 and #64, and a press panel #65 is in a normal state. Press panels #63 to #65 with an environment parameter such as an applied pressure and whether frictional force is generated, which is the same, are compared.

Figure 5:
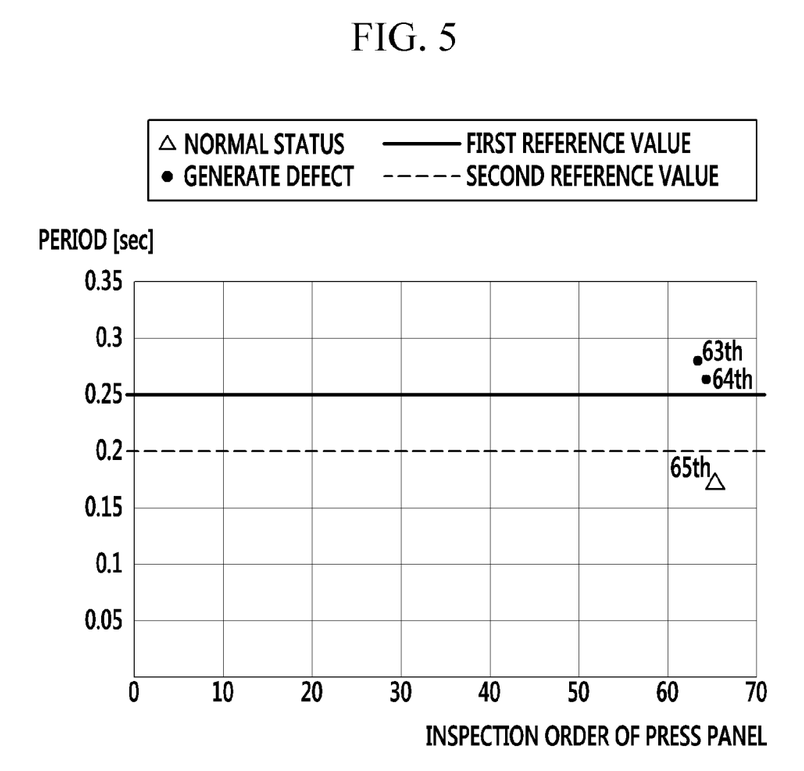
FIG. 5 is a drawing for explaining operations S230 and S240 according to embodiments of the present disclosure.

As the comparison result, as shown in FIG. 5, the press panels have different period values that are differentiated according to whether the press panels are defective. FIG. 5 is a drawing for explaining operations S230 and S240 according to embodiments of the present disclosure. In FIG. 5, the x axis refers to an inspection order of press panels, and the y axis refers to a period of press panels measured by the period measurer 120.

As shown in FIG. 5, press panels #63 and #64 have a comparatively high period value and press panel #65 in a normal state has a comparatively low period value. Simulation proceeds with respect to a plurality of press panels to check two period values for differentiating between a defective press panel and a press panel in a normal state, and a period value for determining a press panel from which a defect is detected is employed as a first reference value and a period value for determining a press panel in a normal state is employed as a second reference value.

A period value between the first reference value and second reference value refers to a range of period values from which a defective press panel and a press panel in a normal state is not accurately determined. The defect existence determination unit 130 may determine whether a press panel with a period between the first reference value and the second reference value is defective using a parameter extracted by the extractor 140.

In addition, the first reference value and the second reference value may have the same value, and the defect existence determination unit 130 may not use a parameter and may determine whether a press panel is defective using one reference value.

Hereinafter, a method for determining whether a press panel having a period between a first reference value and a second reference value is defective using a parameter will be described in detail with reference to FIGS. 6A and 6B. FIGS. 6A and 6B are drawings for explaining operation S260 according to embodiments of the present disclosure.

Figure 6A:
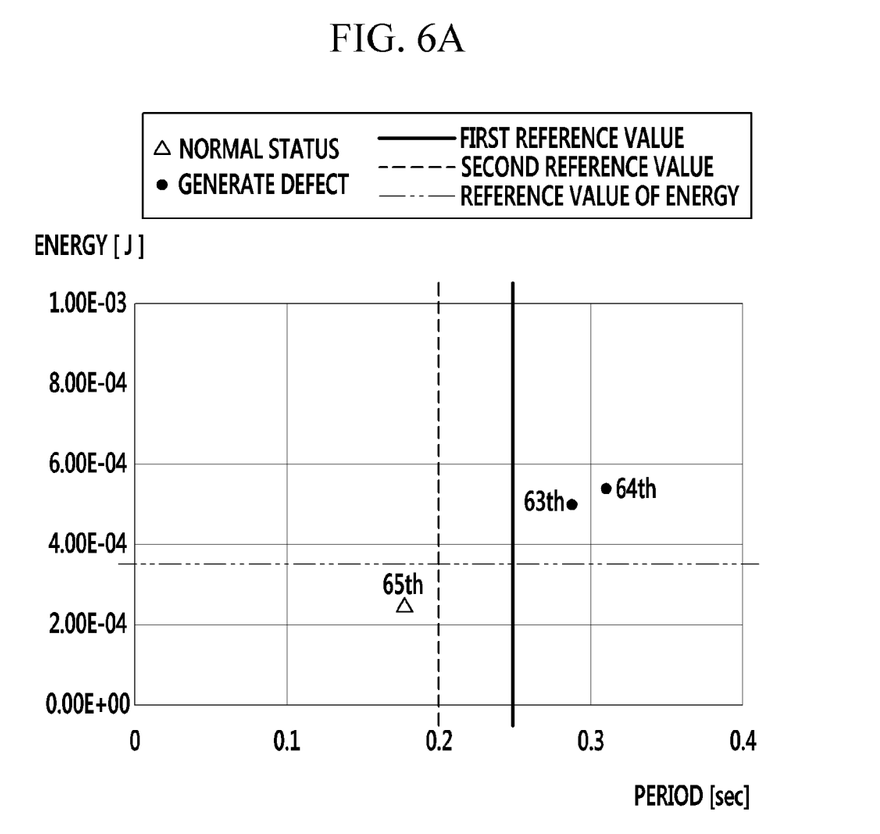
FIGS. 6A and 6B are drawings for explaining operation S260 according to embodiments of the present disclosure.

FIG. 6A is a graph for explaining a method for determining whether a press panel is defective using an energy parameter. As a simulation result, an energy value of a defective press panel is relatively high and an energy value of a press panel in a normal state is relatively low.

Figure 6B:
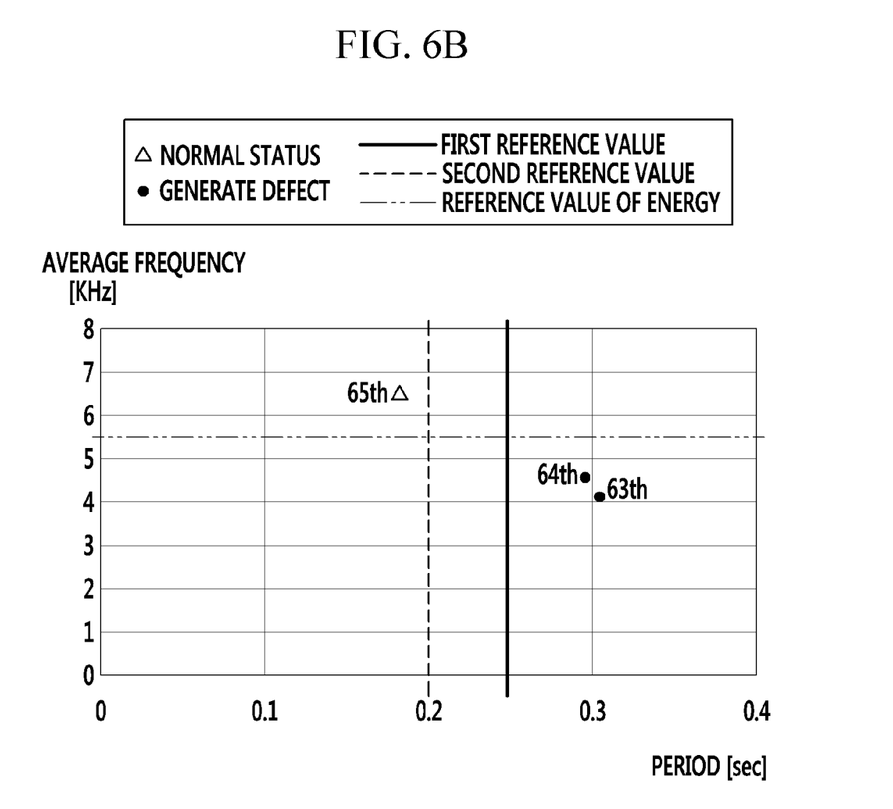

FIG. 6B is a graph for explaining a method for determining whether a press panel is defective using an average frequency parameter. As a simulation result, an average frequency of a defective press panel is relatively is low and an average frequency of a press panel in a normal state is relatively high.

Accordingly, the defect existence determination unit 130 may set a reference value of each parameter according to the simulation result and determine whether a defect is generated in a press panel as a detection target using the reference value of the set parameter.

First, the extractor 140 extracts a parameter with respect to a plurality of press panels, and the defect existence determination unit 130 sets a reference value for differentiating between a press panel in a normal state and a defective press panel. In addition, the extractor 140 extracts a parameter of a press panel as a detection target having a period value between the first reference value and the second reference value, and the defect existence determination unit 130 compares the extracted parameter and a reference value of a predetermined parameter to determine whether a defect is generated in the corresponding press panel.

Among the parameters extracted by the extractor 140, when the number of pulses or energy exceeds a reference value of the number of pulses or a reference number of energy, the corresponding press panel is determined to be defective. In addition, when an average frequency is smaller than a reference value of an average frequency, the corresponding press panel is determined to be defective.

The press panel defect detection apparatus 100 according to the present disclosure may be applied to shearing work for shearing a material by applying a pressure with breaking strength or more to the material, bending work for processing a material to various shapes by applying force to the material to generate bending stress, drawing work for molding a container without a joint while putting the material into a die, or compression work for molding a product with a shape of an internal part of a mold while the material is deformed by applying high compression force to the material so as to detect a defect generated during processing work of various materials. As such, an apparatus and method for detecting a defect of a press panel, as described herein, may be used so as to simply detect a defect generated during press work, and whether a defect is generated may be more accurately determined with respect to a detection target, and defect determination of which is ambiguous, using a parameter.

While this disclosure has been described in connection with what is presently considered to be practical embodiments, it is to be understood that the disclosure is not limited to the disclosed embodiments, but, on the contrary, is intended to cover various modifications and equivalent arrangements included within the spirit and scope of the appended claims.

DESCRIPTION OF SYMBOLS

100: press panel defect detection apparatus
110: acoustic emission sensor unit 120: period measurer
130: defect existence determination unit 140: extractor

What is claimed is:

1. An apparatus for detecting a defect of a press panel, the apparatus comprising:
an acoustic emission sensor unit configured to detect at least one elastic wave signal emitted from the press panel as a detection target during press work;
a period measurer configured to measure a period as a section in which there are consecutive signals with a greater voltage than a threshold voltage among the at least one detected signals; and
a defect existence determination unit configured to determine that a defect is generated in the press panel when the measured period is greater than a first reference value and to determine that the press panel is in a normal state when the measured period is smaller than a second reference value which is smaller than the first reference value.

2. The apparatus of claim 1, wherein:
the first reference value and the second reference value are determined using a period value pre-measured from a plurality of press panels as a comparison target, and
the first reference value and the second reference value refer to a value of a boundary line on distribution of a period of a press panel in which a defect is generated from the comparison target and a period of a press panel in a normal state from the comparison target.

3. The apparatus of claim 1, further comprising:
an extractor configured to extract from the at least one detected signals: i) at least one parameter among the number of pulses with a greater output voltage than the threshold voltage, ii) energy as the sum of areas of pulses with a greater output voltage than a threshold voltage, and iii) an average frequency generated during the period.

4. The apparatus of claim 3, wherein:
the defect existence determination unit is further configured to determine whether the press panel is defective using the at least one extracted parameter when the measured period has a value between the first reference value and the second reference value.

5. The apparatus of claim 4, wherein:
the defect existence determination unit is further configured to:
determine that a defect is generated in a corresponding press panel when the number of pulses and the energy are higher than a reference number among the extracted parameter, and
determine that a defect is generated in the corresponding press panel when the average frequency generated during the period is lower than a reference number.

6. A method for detecting a defect using a press panel defect detection apparatus, the method comprising:
detecting at least one elastic wave signal emitted from the press panel as a detection target during press work;
measuring a period as a section in which there are consecutive signals with a greater voltage than a threshold voltage among the at least one detected signals;
determining that a defect is generated in the press panel when the measured period is greater than a first reference value; and
determining that the press panel is in a normal state when the measured period is smaller than a second reference value which is smaller than the first reference value.

7. The method of claim 6, wherein:
the first reference value and the second reference value are determined using a period value pre-measured from a plurality of press panels as a comparison target, and
the first reference value and the second reference value refer to a value of a boundary line on distribution of a period of a press panel in which a defect is generated from the comparison target and a period of a press panel in a normal state from the comparison target.

8. The method of claim 6, further comprising:
extracting from the at least one detected signal: i) at least one parameter among the number of pulses with a greater output voltage than the threshold voltage, ii) energy as the sum of areas of pulses with a greater output voltage than a threshold voltage, and iii) an average frequency generated during the period.

9. The method of claim 8, wherein the determining that the defect is generated comprises:
determining whether the press panel is defective using the at least one extracted parameter when the measured period has a value between the first reference value and the second reference value.

10. The method of claim 9, wherein the determining that the defect is generated further comprises:
determining that a defect is generated in a corresponding press panel when the number of pulses and the energy are higher than a reference number among the extracted parameter; and
determining that a defect is generated in the corresponding press panel when the average frequency generated during the period is lower than a reference number.

11. A non-transitory computer readable medium containing program instructions for detecting a defect of a press panel, the computer readable medium comprising:
program instructions that measure a period as a section in which there are consecutive signals with a greater voltage than a threshold voltage among at least one elastic wave signal emitted from the press panel detected as a detection target during press work;
program instructions that determine that a defect is generated in the press panel when the measured period is greater than a first reference value; and
program instructions that determine that the press panel is in a normal state when the measured period is smaller than a second reference value which is smaller than the first reference value.

* * * * *